(12) United States Patent
Roeder et al.

(10) Patent No.: US 7,208,427 B2
(45) Date of Patent: Apr. 24, 2007

(54) PRECURSOR COMPOSITIONS AND PROCESSES FOR MOCVD OF BARRIER MATERIALS IN SEMICONDUCTOR MANUFACTURING

(75) Inventors: Jeffrey F. Roeder, Brookfield, CT (US); Chongying Xu, New Milford, CT (US); Bryan C. Hendrix, Danbury, CT (US); Thomas H. Baum, New Fairfield, CT (US)

(73) Assignee: Advanced Technology Materials, Inc., Danbury, CT (US)

( * ) Notice: Subject to any disclaimer, the term of this patent is extended or adjusted under 35 U.S.C. 154(b) by 247 days.

(21) Appl. No.: 10/643,110

(22) Filed: Aug. 18, 2003

(65) Prior Publication Data

US 2005/0042888 A1 Feb. 24, 2005

(51) Int. Cl.
*H01L 21/31* (2006.01)
*H01L 21/469* (2006.01)

(52) U.S. Cl. ............... 438/791; 438/794; 257/E21.493; 257/E23.167; 427/255.18; 556/400

(58) Field of Classification Search ........ 438/700, 438/791–794; 427/384, 255.18, 255.27, 427/255.28; 257/E21.493, E23.167, E21.487, 257/E23.118; 556/170, 400, 413
See application file for complete search history.

(56) References Cited

U.S. PATENT DOCUMENTS

| | | | | |
|---|---|---|---|---|
| 3,467,686 A | * | 9/1969 | Creamer | 556/410 |
| 4,499,198 A | * | 2/1985 | Pullukat et al. | 502/104 |
| 4,783,430 A | * | 11/1988 | Su | 501/96.2 |
| 4,788,309 A | * | 11/1988 | Laine et al. | 556/412 |
| 5,578,530 A | * | 11/1996 | Muroyama et al. | 438/791 |
| 5,603,988 A | * | 2/1997 | Shapiro et al. | 427/248.1 |
| 5,675,028 A | * | 10/1997 | Neumayer et al. | 552/4 |
| 5,908,947 A | * | 6/1999 | Vaartstra | 556/42 |
| 6,320,213 B1 | * | 11/2001 | Kirlin et al. | 257/295 |
| 6,352,921 B1 | * | 3/2002 | Han et al. | 438/638 |
| 6,379,748 B1 | * | 4/2002 | Bhandari et al. | 427/255.394 |
| 6,445,023 B1 | * | 9/2002 | Vaartstra et al. | 257/295 |
| 6,552,209 B1 | * | 4/2003 | Lei et al. | 556/42 |
| 6,786,936 B2 | * | 9/2004 | Vaartstra | 29/25.01 |
| 2002/0081385 A1 | * | 6/2002 | Kron et al. | 427/384 |
| 2002/0175393 A1 | * | 11/2002 | Baum et al. | 257/506 |
| 2002/0187644 A1 | * | 12/2002 | Baum et al. | 438/700 |

FOREIGN PATENT DOCUMENTS

JP 2000036473 * 2/2000

* cited by examiner

*Primary Examiner*—Caridad Everhart
(74) *Attorney, Agent, or Firm*—Steven J. Hultquist; Intellectual Property/Technology Law; Margaret Chappuis

(57) ABSTRACT

Metalorganic precursors of the formula:

$$(R_1R_2N)_{a-b}MX_b$$

wherein: M is the precursor metal center, selected from the group of Ta, Ti, W, Nb, Si, Al and B; a is a number equal to the valence of M; $1 \leq b \leq (a-1)$; $R_1$ and $R_2$ can be the same as or different from one another, and are each independently selected from the group of H, $C_1$–$C_4$ alkyl, $C_3$–$C_6$ cycloalkyl, and $R^0{}_3Si$, where each $R^0$ can be the same or different and each $R^0$ is independently selected from H and $C_1$–$C_4$ alkyl; and X is selected from the group of chlorine, fluorine, bromine and iodine. Precursors of such formula are useful for chemical vapor deposition (MOCVD) of conductive barrier materials in the manufacture of microelectronic device structures, e.g., by atomic layer chemical vapor deposition on a substrate bearing nitrogen-containing surface functionality. Further described is a method of forming $Si_3N_4$ on a substrate at low temperature, e.g., using atomic layer chemical vapor deposition (ALCVD).

43 Claims, No Drawings

PRECURSOR COMPOSITIONS AND PROCESSES FOR MOCVD OF BARRIER MATERIALS IN SEMICONDUCTOR MANUFACTURING

FIELD OF THE INVENTION

The present invention relates to precursor compositions and processes for metalorganic chemical vapor deposition (MOCVD) of barrier materials in the manufacture of microelectronic device structures.

DESCRIPTION OF THE RELATED ART

As critical dimensions of backend microelectronic interconnect wiring continue to shrink and aspect ratios of vias and lines increase in the manufacture of semiconductor products, there is a need for conductive barriers with improved conformality characteristics.

MOCVD using amide-based precursors, such as tetrakis (diethylamino)titanium (TDEAT), tetrakis(dimethylamino) titanium (TDMAT), and the like, afford increased conformality of deposited material over physical vapor deposition (PVD) methods, as a consequence of their surface reaction limited kinetics. Nonetheless, deposition processes characterized by surface reaction limited kinetics may not enable the achievement of sufficient conformality in future applications involving increasingly small (e.g., <30 nanometers) feature dimensions and correspondingly thin barrier layer films.

Atomic layer chemical vapor deposition (ALCVD) has been investigated for such dimensionally rigorous future applications and has been demonstrated to produce highly conformal films in very fine features having dimensions on the order of 50 nanometers with high abstract ratios. In the current state of development of the art, halide-based sources have been employed for ALCVD, including the use of titanium chlorides and titanium bromides for deposition of titanium nitride, and the use of tantalum chlorides and tantalum bromides for deposition of tantalum nitride.

Such halide precursors have a robust reaction with an =NH or an —NH$_2$ terminated surface, producing a halide-terminated surface that is resistant to further reaction and on which the sticking coefficient is low. A significant deficiency of such halide precursors, however, is the formation of large amounts of ammonium halides as a product of the reaction of the halide metal source with ammonia to produce the nitride film. This is particularly the case when the halide is chlorine, since ammonium chloride is a low volatility solid at low temperatures and tends to foul downstream vacuum lines and create significant maintenance issues for the CVD tool.

ALCVD has been attempted with amide-based precursors, but the associated reactions are not robustly self-limiting, as is desired for high conformality, high quality films.

The art therefore remains in need of improved precursors and deposition processes for the formation of very thin, high-conformality barrier films for the manufacture of semiconductor products.

SUMMARY OF THE INVENTION

The present invention relates to precursor compositions and processes for metalorganic chemical vapor deposition (MOCVD) of barrier materials in the manufacture of microelectronic device structures.

In one aspect, the invention relates to a process for forming a nitride material on a substrate, comprising volatilizing a nitrogen-containing precursor to form a corresponding precursor vapor, and contacting the substrate with the precursor vapor under chemical vapor deposition conditions to deposit said nitride material, wherein the precursor comprises a compound of formula (I):

$$(R_1R_2N)_{a-b}MX_b \qquad (I)$$

wherein:

M is selected from the group of Ta, Ti, W, Nb, Si, Al and B;

a is a number equal to the valence of M;

$1 \leq b \leq (a-1)$;

R$_1$ and R$_2$ can be the same as or different from one another, and are each independently selected from the group of H, C$_1$–C$_4$ alkyl, C$_3$–C$_6$ cycloalkyl, and R$^0$$_3$Si, where each R$^0$ can b the same or different and each R$^0$ is independently selected from H and C$_1$–C$_4$ alkyl; and X is selected from the group of chlorine, fluorine, bromine and iodine.

In the foregoing formula (I), when M is selected to be silicon, the silicon species comprehended by such selection can be Si per se, or alternatively, Si—Si (disilane).

Another aspect of the invention relates to a process for forming Si$_3$N$_4$ material on a nitrogen-functionalized substrate, comprising volatilizing a silicon-containing precursor to form a corresponding precursor vapor, and contacting the substrate with the precursor vapor under chemical vapor deposition conditions to deposit silicon material thereon, wherein said precursor comprises a compound of formula (II):

$$R_mR'_nSiH_yX_{4-(m+n+y)} \qquad (II)$$

wherein:

X is Cl or Br;

m, n and y can each be the same as or different from each other, and each is independently from 0 to 3 inclusive; and R and R' are the same as or different from one another, and each is independently selected from the group of H, C$_1$–C$_4$ alkyl, and C$_3$–C$_6$ cycloalkyl.

Still another aspect of the invention relates to a metalorganic precursor of formula (I):

$$(R_1R_2N)_{a-b}MX_b \qquad (I)$$

wherein:

M is selected from the group of Ta, Ti, W, Nb, Si, Al and B;

a is a number equal to the valence of M;

$1 \leq b \leq (a-1)$;

R$_1$ and R$_2$ can be the same as or different from one another, and are each independently selected from the group of H, C$_1$–C$_4$ alkyl, C$_3$–C$_6$ cycloalkyl, and R$^0$$_3$Si, where each R$^0$ can be the same or different and each R$^0$ is independently selected from H and C$_1$–C$_4$ alkyl; and X is selected from the group of chlorine, fluorine, bromine and iodine.

Yet another aspect of the invention relates to a metalorganic precursor composition comprising a compound of formula (I):

$$(R_1R_2N)_{a-b}MX_b \qquad (I)$$

wherein:

M is selected from the group of Ta, Ti, W, Nb, Si, Al and B;

a is a number equal to the valence of M;

$1 \leq b \leq (a-1)$;

$R_1$ and $R_2$ can be the same as or different from one another, and are each independently selected from the group of H, $C_1-C_4$ alkyl, $C_3-C_6$ cycloalkyl, and $R^0_3Si$, where each $R^0$ can be the same or different and each $R^0$ is independently selected from H and $C_1-C_4$ alkyl; and X is selected from the group of chlorine, fluorine, bromine and iodine.

In another aspect, the invention relates to a method of forming $Si_3N_4$ on a surface of a substrate by an ALCVD process, comprising functionalizing the surface with a nitrogen-containing functionality to form a functionalized surface, and contacting the functionalized surface with a silane halide compound under reaction conditions producing $Si_3N_4$ as a reaction product on the surface of the substrate, wherein the silane halide has the formula:

$$R_m R'_n SiH_y X_{4-(m+n+y)}$$

wherein:

X is Cl or Br;

m, n and y can each be the same as or different from each other, and each is independently from 0 to 3 inclusive; and R and R' are the same as or different from one another, and each is independently selected from the group of H, $C_1-C_4$ alkyl, and $C_3-C_6$ cycloalkyl.

Other aspects, features and embodiments of the invention will be more fully apparent from the ensuing disclosure and appended claims.

DETAILED DESCRIPTION OF THE INVENTION, AND PREFERRED EMBODIMENTS THEREOF

The present invention is based on the discovery of new precursors that can be usefully employed to form TiN, TaN, and corresponding Si-substituted and Al-substituted forms of such nitrides (e.g., silicon titanium nitride, silicon tantalum nitride, aluminum titanium nitride, and aluminum tantalum nitride), wherein the nitride material has a reduced halide content relative to nitride films formed with conventionally employed halogen-containing precursor materials.

In one embodiment of the process of the invention, the precursor is adsorbed on the surface of the structure to be coated and subsequently reacted with ammonia or other co-reactant nitrogen source to create a nitride film, and these adsorption and reaction steps are repeated in alternating sequence until the desired nitride barrier film thickness is achieved, optionally with an intervening purge cycle in which an inert gas is employed to sweep the precursor from the deposition system.

The ammonia or other co-reactant nitrogen source can be injected into the deposition system for reaction at the deposition locus, e.g., substrate surface on which the barrier layer is to be formed, or alternatively, the ammonia or other co-reactant nitrogen source can be present as a surface functionality on the substrate surface, thereby forming a substantially monomolecular layer of the reactive functionality, whereby subsequent reaction with the precursor forms the nitride material of a corresponding monomolecular character.

In a specific embodiment, one of the precursor and co-reactant species is flowed in a continuous or sustained manner, with pulsing of the other one of the precursor and co-reactant species, in a pulsed injection mode.

A further embodiment of the invention provides Si—, Al— or B-substituted films, wherein silicon, aluminum or boron source reagent is co-injected with a metal nitride source reagent. Boron source reagents for such purpose include borane, decaborane, alkylboranes and amidoboranes.

In another embodiment, Si— or Al-substituted films are provided by use of a Si— or Al-substituted metalorganic (metal nitride) source reagent.

In yet another embodiment, a Si, Al or B source is injected toward the end of the deposition process, from a mixed metalorganic-halide source reagent, or from a silane, alane or borane source reagent, to form the Si—, Al— or B-substituted nitride material.

A further embodiment of the invention involves injecting the Si or Al source alternatingly with the Ti or Ta, to form nano-layered films or to prevent reactions between species in the gas phase.

The nitride material formed on the substrate in the practice of the present invention is usefully employed as a barrier material in the manufacture of semiconductor products, e.g., as a barrier layer between electrode layers and underlying oxide material, to prevent or minimize migration of species that would compromise the integrity and/or operability of the semiconductor product.

The invention relates in one compositional aspect to precursors of the formula:

$$(R_1R_2N)_{a-b}MX_b \tag{I}$$

wherein:

M is selected from the group of Ta, Ti, W, Nb, Si, Al and B;

a is a number equal to the valence of M;

$1 \leq b \leq (a-1)$;

$R_1$ and $R_2$ can be the same as or different from one another, and are each independently selected from the group of H, $C_1-C_4$ alkyl, $C_3-C_6$ cycloalkyl, and $R^0_3Si$, where each $R^0$ can be the same or different and each $R^0$ is independently selected from H and $C_1-C_4$ alkyl; and X is selected from the group of chlorine, fluorine, bromine and iodine.

Illustrative examples of precursors of the foregoing formula (I) include, without limitation:

$(EtHN)_{6-b}WX_b$ wherein b is 1 or 2;

$(EtMeN)_{6-b}WX_b$ wherein b is 1 or 2;

$(Me_2N)_{6-b}WX_b$ wherein b is 1 or 2;

$(Et_2N)_{6-b}WX_b$ wherein b is 1 or 2;

$(EtHN)_{5-b}MX_b$ wherein M is Ta or Nb, and b is 1 or 2;

$(EtMeN)_{5-b}MX_b$ wherein M is Ta or Nb, and b is 1 or 2;

$(Me_2N)_{5-b}MX_b$ wherein M is Ta or Nb, and b is 1 or 2;

$(Et_2N)_{5-b}MX_b$ wherein M is Ta or Nb, and b is 1 or 2;

$(EtHN)_{4-b}TiX_b$ wherein b is from 1 to 2 inclusive;

$(EtMeN)_{4-b}TiX_b$ wherein b is from 1 to 2 inclusive;

$(Me_2N)_{4-b}TiX_b$ wherein b is from 1 to 2 inclusive;

$(Et_2N)_{4-b}TiX_b$ wherein b is from 1 to 2 inclusive;

$(EtHN)_{4-b}SiX_b$ wherein b is from 1 to 2 inclusive;

$(EtMeN)_{4-b}SiX_b$ wherein b is from 1 to 2 inclusive;

$(Me_2N)_{4-b}SiX_b$ wherein b is from 1 to 2 inclusive;

$(Et_2N)_{4-b}SiX_b$ wherein b is from 1 to 2 inclusive;

$(Me_2N)_{3-b}(X)_bSi$—$Si(X)_b(NMe_2)_{3-b}$ wherein b is 1 or 2; and $(Et_2N)_{3-b}(X)_bSi$—$Si(X)_b(NEt_2)_{3-b}$ wherein b is 1 or 2.

The precursors of formula (I) that include the silyl groups, $R^0_3Si$, are usefully employed for forming silicon-containing nitride materials, e.g., silicon titanium nitride films. Illustrative examples of such precursors include, without limitation:

[(Me$_3$Si)$_2$N]$_{4-b}$TiX$_b$ wherein b is 1 or 2, and X is Cl, Br, F or I;

[(Me$_3$Si)$_2$N]$_{5-b}$MX$_b$ wherein b is 2 or 3, X is Cl, Br, F or I, and M is Ta or Nb;

[(Me$_3$Si)$_2$N]$_{6-b}$WX$_b$ wherein b is 1 or 2, and X is Cl, Br, F or I.

The compounds of formula (I) are highly useful in the formation of titanium nitride and tantalum nitride barrier films.

The compounds of formula (I) can be employed to form corresponding nitride material layers on substrates, by a multiple step process, in which the precursor of formula (I) is contacted with a substrate in a first step, to adsorb the precursor on the substrate, followed by contacting of the adsorbed precursor on the substrate with a co-reactant nitrogen source that is reactive with the precursor to form the desired nitride material on the substrate, as a second step.

Such first and second contacting steps can be carried out alternatingly and repetitively with respect to one another, for sufficient time and sufficient number of repetitions to form the nitride material at a predetermined thickness, e.g., a thickness in a range of from about 1 to about 100 nanometers.

The co-reactant nitrogen source can be of any suitable type, e.g., ammonia, alkyl amines, boranes, borazines, compounds containing nitrogen-to-nitrogen bonds, such as hydrazine, dialkyl hydrazine and tetraalkyl hydrazine, etc., wherein alkyl in such compounds is selected from $C_1$–$C_8$ alkyl and more preferably from $C_1$–$C_4$ alkyl, and in polyalkyl compounds each alkyl substituent is independently selected from $C_1$–$C_8$ alkyl or more preferably from $C_1$–$C_4$ alkyl. Hydrogen may also be used as a co-reactant species in some embodiments of the invention, and hydrogen may be employed in combination with a nitrogen source compound such as ammonia, as a H$_2$/NH$_3$ mixture.

The above-described process can also be carried out with an intervening step between the aforementioned first and second steps, in which the substrate is purged of first step gases prior to commencement of the second step. Such intermediate purge step can be conducted with a suitable purge gas medium, e.g., including an inert gas, a reducing gas, or other suitable species effective for such purging operation. Illustrative purge gas species include, without limitation, argon, nitrogen, helium, N$_2$O, hydrogen, and compatible mixtures including two or more of the foregoing gases.

In a further aspect of the invention, a metal halide of formula (I) can be employed in combination with a silicon source reagent, as a multicomponent precursor, to produce a silicon-containing nitride material on the substrate. The silicon source reagent can be of any suitable type, including for example, without limitation, silane, alkylsilanes, halosilanes, and alkylhalosilanes, wherein the alkyl moiety is $C_1$–$C_4$ alkyl, and halo is Cl, Br, F or I.

In corresponding manner, the metal halide of formula (I) can be employed in combination with an aluminum source reagent, as a multicomponent precursor, to produce an aluminum-containing nitride material on the substrate. The aluminum source reagent can be of any suitable type, including for example, without limitation, alane, alkylalanes, haloalanes and alkylhaloalanes, wherein the alkyl moiety is $C_1$–$C_4$ alkyl, and halo is Cl, Br, F or I.

In the previously described two-step process for forming the nitride material on the substrate, the process can be carried out in a pulsed manner, wherein one of the first and second steps is conducted in a pulsed fashion relative to the other step.

As a further process variant, the general process described hereinabove can be conducted with the augmentation of the precursor in a latter portion of the nitride material deposition process, by adding to the precursor composition (containing the compound of formula (I)) a silicon source reagent and/or an aluminum source reagent, to form a silicon- and/or aluminum-substituted nitride material upper layer in the deposited material.

Suitable reaction conditions for precursor contacting in the processes of the invention are readily determinable within the skill of the art for a given precursor and co-reactant species, based on the disclosure herein and routine empirical determination using varying temperatures, pressures, flow rates and precursor/co-reactant species. In one embodiment of the invention, the precursor/co-reactant reaction is advantageously carried out in a temperature range of from about 150 to about 600° C., pressure on the order of from about 0.2 to about 200 torr, and flow rates in a range of from about 0.1 to about 10 sccm for precursors and from about 10 to about 10,000 sccm for co-reactant reagents.

The invention also relates to a low temperature Si$_3$N$_4$ ALCVD process, in which Si$_3$N$_4$ is formed on a surface of a substrate by an ALCVD process. In the process of the invention, the surface is first functionalized with a nitrogen-containing functionality to form a functionalized surface. The functionalized surface then is contacted with a silane halide compound under reaction conditions producing Si$_3$N$_4$ as a reaction product on the surface of the substrate, using a silane halide of the formula (II):

$$R_mR'_nSiH_yX_{4-(m+n+y)} \tag{II}$$

wherein:

X is Cl or Br;

m, n and y can each be the same as or different from each other, and each is independently from 0 to 3 inclusive; and R and R' are the same as or different from one another, and each is independently selected from the group of H, $C_1$–$C_4$ alkyl, and $C_3$–$C_6$ cycloalkyl.

As used in such context, the term "low temperature" means temperature in a range of from about 150 to about 400° C.

Illustrative examples of silane halide precursors for such low temperature formation of Si$_3$N$_4$ include, without limitation: ClSiH$_3$; H$_2$SiCl$_2$; Me$_3$SiCl; t-Bu$_2$SiCl$_2$; and the like.

Precursors of the present invention are also useful in application to continuous MOCVD processes, wherein all reactants and precursors are introduced at a nominally constant rate. In such case, the partially halogenated precursors of the present invention have an advantage over alkylamido sources, in that they nucleate well on low k or other dielectric surfaces. As used herein, "low k" means a dielectric constant value that does not exceed about 3.9.

The partially halogenated precursors of the present invention also have an advantage over fully halogenated precursors in that they produce less ammonium halide in the effluent waste steam from chemical vapor deposition chamber.

The precursors of formula (I) can be readily synthesized by the following reaction:

$$MX_a + b(R_1R_2N)Li \rightarrow (R_1R_2N)_{a-b}MX_b + bLiX$$

wherein M, X, a, b, R$_1$ and R$_2$ are as defined hereinabove for formula (I). Such synthesis reaction can be carried out under any suitable temperature and pressure conditions, as readily determinable without undue effort, within the skill of the art.

The precursors of the invention can be used to form nitride barrier layers on semiconductor substrates, in the manufacture of microelectronic devices or precursor structures therefor. The formation can be carried out by chemical vapor deposition using conventional MOCVD equipment and general process techniques.

In one preferred aspect of the invention, the chemical vapor deposition process that is employed to form the nitride material on the substrate comprises atomic layer chemical vapor deposition (ALCVD), and involves contacting of the metalorganic precursor with a surface functionalized with a nitrogen-containing functionality, such as =NH and/or —NH$_2$, which reacts with the metal moiety of the precursor to form a metal nitride molecular monolayer on the substrate surface. The nitrogen-functionalized surface in a preferred embodiment is an aminated surface. The film-forming operation may be continued as desired with further contacting of the substrate with a nitrogen-containing reactant such as ammonia, amide, or other reagent of suitable reactivity, and precursor, so that reaction between the nitrogen-source co-reactant and the precursor forms additional metal nitride material on the substrate. This process can be continued as necessary or desired, to achieve a predetermined thickness of the metal nitride layer. For example, a titanium nitride or a silicon titanium nitride film can be formed by such technique, having a thickness in a range of from about 1 to about 100 nanometers.

In specific embodiments, ALCVD processes in accordance with the present invention can be carried out at temperatures in a range of from about 150 to about 600° C., and at pressures of from about 0.2 to about 200 torr, with appropriate flow rates and concentrations of the source reagents and any carrier gas components employed in the ALCVD process.

The ALCVD process of the invention in another aspect can be carried out to form the deposited film from multiple layers of adsorbed species under similar deposition conditions. In yet another aspect, the film may be formed in a continuous manner without pulsing.

While the invention has been described herein in reference to specific aspects, features and illustrative embodiments of the invention, it will be appreciated that the utility of the invention is not thus limited, but rather extends to and encompasses numerous other variations, modifications and alternative embodiments, as will suggest themselves to those of ordinary skill in the field of the present invention, based on the disclosure herein. Correspondingly, the invention as hereinafter claimed is intended to be broadly construed and interpreted, as including all such variations, modifications and alternative embodiments, within its spirit and scope.

What is claimed is:

1. A process for forming a nitride material on a substrate, including the steps of volatilizing a nitrogen-containing precursor to form a corresponding precursor vapor, and contacting the substrate with the precursor vapor under chemical vapor deposition conditions to deposit said nitride material, wherein said precursor comprises a compound of formula (I):

$$(R_1R_2N)_{a-b}MX_b \qquad (I)$$

wherein:
M is selected from the group of Ta, Ti, W, Nb, Al and B;
a is a number equal to the valence of M;
$1 \leq b \leq (a-1)$;
$R_1$ and $R_2$ can be the same as or different from one another, and are each independently selected from the group of H, $C_1$–$C_4$ alkyl, $C_3$–$C_6$ cycloalkyl, and, when M is W, Nb, Al or B, $R^0{}_3$Si, where each $R^0$ can be the same or different and each $R^0$ is independently selected from H and $C_1$–$C_4$ alkyl; and
X is selected from the group of chlorine, fluorine, bromine and iodine;
but excluding compounds of the formula $(Me_2N)_{4-b}TiX_b$ wherein b is from 1 to 2 inclusive.

2. The process of claim 1, wherein M is selected from the group consisting of Ta and Ti.

3. The process of claim 1, wherein M is Ta.

4. The process of claim 1, wherein M is Ti.

5. The process of claim 1, wherein said precursor further comprises an aluminum source reagent, whereby said nitride material further comprises aluminum therein, wherein said aluminum source reagent comprises an alane reagent selected from the group consisting of alane, alkylalanes, haloalanes and alkylhaloalanes, wherein alkyl is $C_1$–$C_4$ alkyl and halo is Cl, Br, F or I.

6. The process of claim 1, wherein said precursor comprises a boron source, wherein said boron source reagent comprises a borane selected from the group consisting of borane, decaborane, alkylboranes and amidoboranes.

7. The process of claim 1, wherein the contacting in a latter portion thereof comprises adding further source reagent to said compound of formula (I) to constitute said precursor, wherein said further source reagent comprises at least one reagent selected from the group consisting of silicon source reagents and aluminum source reagents.

8. The process of claim 1, wherein said precursor comprises a compound selected from the group consisting of:
(EtHN)$_{6-b}$WX$_b$ wherein b is from 1 to 2 inclusive;
(EtMeN)$_{6-b}$WX$_b$ wherein b is from 1 to 2 inclusive;
(Me$_2$N)$_{6-b}$WX$_b$ wherein b is from 1 to 2 inclusive;
(Et$_2$N)$_{6-b}$WX$_b$ wherein b is from 1 to 2 inclusive;
(EtHN)$_{5-b}$MX$_b$ wherein M is Ta or Nb, and b is 1 or 2;
(EtMeN)$_{5-b}$MX$_b$ wherein M is Ta or Nb, and b is 1 or 2;
(Me$_2$N)$_{5-b}$MX$_b$ wherein M is Ta or Nb, and b is 1 or 2;
(Et$_2$N)$_{5-b}$MX$_b$ wherein M is Ta or Nb, and b is 1 or 2;
(EtHN)$_{4-b}$TiX$_b$ wherein b is from 1 to 2 inclusive;
(EtMeN)$_{4-b}$TiX$_b$ wherein b is from 1 to 2 inclusive;
(Et$_2$N)$_{4-b}$TiX$_b$ wherein b is from 1 to 2 inclusive;
[(Me$_3$Si)$_2$N]$_{5-b}$MX$_b$ wherein b is 2 or 3, X is Cl, Br, F or I, and M is Nb; and
[(Me$_3$Si)$_2$N]$_{6-b}$WX$_b$ wherein b is 1 or 2, and X is Cl, Br, F or I.

9. The process of claim 1, wherein said precursor comprises a compound selected from the group consisting of:
[(Me$_3$Si)$_2$N]$_{5-b}$MX$_b$ wherein b is 2 or 3, X is Cl, Br, F or I, and M is Nb; and
[(Me$_3$Si)$_2$N]$_{6-b}$WX$_b$ wherein b is 1 or 2, and X is Cl, Br, F or I.

10. The process of claim 1, wherein said precursor further comprises a silicon source reagent, whereby said nitride material further comprises silicon therein, wherein said silicon source reagent comprises a silane reagent selected from the group consisting of silane, alkylsilanes, halosilanes, and alkylhalosilanes, wherein alkyl is $C_1$–$C_4$ alkyl and halo is Cl, Br, F or I.

11. The process of claim 10, wherein said nitride material comprises titanium silicon nitride.

12. The process of claim 1, wherein said nitride material comprises a migration barrier on said substrate.

13. The process of claim 12, wherein said nitride material comprises titanium nitride having a thickness in a range of from about 1 to about 100 nanometers.

14. The process of claim 1, wherein said contacting is carried out to adsorb precursor on the substrate as a first step, and a co-reactant nitrogen source that is reactive with the adsorbed precursor to form said nitride material, is contacted with the adsorbed precursor under reaction conditions for forming said nitride material, as a second step.

15. The process of claim 14, wherein said co-reactant nitrogen source is selected from the group consisting of ammonia, alkyl amines, boranes, borazines, hydrazine, dialkyl hydrazine and tetraalkyl hydrazine.

16. The process of claim 14, wherein one of said first and second steps is carried out in a pulsed manner relative to the other step.

17. The process of claim 14, wherein the first and second steps are carried out alternatingly and repetitively with respect to one another, for sufficient number of repetitions to form said nitride material at a predetermined thickness.

18. The process of claim 17, wherein said predetermined thickness is in a range of from about 1 to about 100 nanometers.

19. The process of claim 14, further comprising between said first and second steps an intervening step of contacting the substrate with a purge gas to purge the substrate of first step gases prior to commencement of the second step.

20. The process of claim 19, wherein said purge gas comprises a gas selected from the group consisting of argon, nitrogen, helium, $N_2O$, hydrogen, and compatible combinations of two or more of the foregoing gases.

21. A process for forming $Si_3N_4$ material on a nitrogen-functionalized substrate, wherein the nitrogen functionalized substrate is formed by the process comprising:

forming a nitride material on a substrate, including the steps of volatilizing a nitrogen-containing precursor to form a corresponding precursor vapor, and contacting the substrate with the precursor vapor under chemical vapor deposition conditions to deposit said nitride material, wherein said precursor comprises a compound of formula (I):

$$(R_1R_2N)_{a-b}MX_b \quad (I)$$

wherein:
M is selected from the group of Ta, Ti, W, Nb, Si, Al and B;
a is a number equal to the valence of M;
$1 \leq b \leq (a-1)$;
$R_1$ and $R_2$ can be the same as or different from one another, and are each independently selected from the group of H, $C_1$–$C_4$ alkyl, $C_3$–$C_6$ cycloalkyl, and, when M is W, Nb, Al or B, $R^0{}_3Si$, where each $R^0$ can be the same or different and each $R^0$ is independently selected from H and $C_1$–$C_4$ alkyl; and
X is selected from the group of chlorine, fluorine, bromine and iodine:
but excluding compounds of the formula $(Me_2N)_{4-b}TiX_b$ wherein b is from 1 to 2 inclusive; and
the process for forming $Si_3N_4$ material comprises:
volatilizing a silicon-containing precursor to form a corresponding precursor vapor, and contacting the substrate with the precursor vapor under chemical vapor deposition conditions to deposit silicon material thereon, wherein said precursor comprises a compound of formula (II):

$$R_mR'_nSiH_yX_{4-(m+n+y)} \quad (II)$$

wherein:
X is Cl or Br,
m, n and y can each be the same as or different from each other, and each is independently from 0 to 3 inclusive; and
R and R' are the same as or different from one another, and each is independently selected from the group of H, $C_1$–$C_4$ alkyl, and $C_3$–$C_6$ cycloalkyl.

22. The process of claim 21, wherein said nitrogen-functionalized substrate comprises a surface functionalized with =NH and/or —$NH_2$ functionality.

23. The process of claim 21, wherein said compound of formula (II) is selected from the group consisting of:
ClSiH$_3$;
H$_2$SiCl$_2$;
Me$_3$SiCl; and
t-Bu$_2$SiCl$_2$.

24. The process of claim 21, wherein said nitrogen-functionalized substrate comprises an aminated substrate.

25. The process of claim 21, wherein said chemical vapor deposition comprises ALCVD.

26. The process of claim 21, wherein said nitrogen-functionalized substrate comprises a dielectric surface.

27. The process of claim 21, wherein said nitrogen-functionalized substrate comprises a low k surface.

28. A metalorganic precursor of formula (I):

$$(R_1R_2N)_{a-b}MX_b \quad (I)$$

wherein:
M is selected from the group of Ta, Ti, W, Nb, and B;
a is a number equal to the valence of M;
$1 \leq b \leq (a-1)$;
$R_1$ and $R_2$ can be the same as or different from one another, and are each independently selected from the group of H $C_1$–$C_4$ alkyl, $C_3$–$C_6$ cycloalkyl, and, when M is W, Nb or B, $R^0{}_3Si$, where each $R^0$ can be the same different and each $R^0$ is independently selected from H and $C_1$–$C_4$ alkyl; and
X is selected from the group of chlorine, fluorine, bromine and iodine;
but excluding compounds of the formula $(Me_2N)_{4-b}TiX_b$ wherein b is from 1 to 2 inclusive.

29. The metalorganic precursor of claim 28, wherein M is selected from the group consisting of Ta and Ti.

30. The metalorganic precursor of claim 28, wherein M is Ta.

31. The metalorganic precursor of claim 28, wherein M is Ti.

32. The metalorganic precursor of claim 28, selected from the group consisting of:
(EtHN)$_{6-b}$WX$_b$ wherein b is from 1 to 2 inclusive;
(EtMeN)$_{6-b}$WX$_b$ wherein b is from 1 to 2 inclusive;
(Me$_2$N)$_{6-b}$WX$_b$ wherein b is from 1 to 2 inclusive;
(Et$_2$N)$_{6-b}$WX$_b$ wherein b is from 1 to 2 inclusive;
(EtHN)$_{5-b}$MX$_b$ wherein M is Ta or Nb, and b is 1 or 2;
(EtMeN)$_{5-b}$MX$_b$ wherein M is Ta or Nb, and b is 1 or 2;
(Me$_2$N)$_{5-b}$MX$_b$ wherein M is Ta or Nb, and b is 1 or 2;
(Et$_2$N)$_{5-b}$MX$_b$ wherein M is Ta or Nb, and b is 1 or 2;
(EtHN)$_{4-b}$TiX$_b$ wherein b is from 1 to 2 inclusive;
(EtMeN)$_{4-b}$TiX$_b$ wherein b is from 1 to 2 inclusive;
(Et$_2$N)$_{4-b}$TiX$_b$ wherein b is from 1 to 2 inclusive;

[(Me₃Si)₂N]₅₋ᵦMXᵦ wherein b is 2 or 3, X is Cl, Br, F or I, and M is Nb; and

[(Me₃Si)₂N]₆₋ᵦWXᵦ wherein b is 1 or 2, and X is Cl, Br, F or I.

33. The metalorganic precursor of claim 28, wherein said precursor is selected from the group consisting of:

[(Me₃Si)₂N]₅₋ᵦMXᵦ wherein b is 2 or 3, X is Cl, Br, F or I, and M is Nb and

[(Me₃Si)₂N]₆₋ᵦWXᵦ wherein b is 1 or 2, and X is Cl, Br, F or I.

34. A metalorganic precursor composition comprising a compound of formula (I):

wherein:
M is selected from the group of Ta, Ti, W, Nb, and B;
a is a number equal to the valence of M;
$1 \leq b \leq (a-1)$;
R₁ and R₂ can be the same as or different from one another, and are each independently selected from the group of H, C₁–C₄ alkyl, C₃–C₆ cycloalkyl, and, when M is W, Nb or B, R⁰₃Si, where each R⁰ can be the same or different and each R⁰ is independently selected from H and C₁–C₄ alkyl; and
X is selected from the group of chlorine, fluorine, bromine and iodine;
but excluding compounds of the formula (Me₂N)₄₋ᵦTiXᵦ wherein b is from 1 to 2 inclusive.

35. The composition of claim 34, further comprising a silicon source reagent, wherein said silicon source reagent comprises a silane reagent selected from the group consisting of silane, alkylsilanes, halosilanes, and alkylhalosilanes, wherein alkyl is C₁–C₄ alkyl and halo is Cl, Br, F or I.

36. The composition of claim 34, further comprising an aluminum source reagent, wherein said aluminum source reagent comprises an alane reagent selected from the group consisting of alane, alkylalanes, haloalanes and alkylhaloalanes, wherein alkyl is C₁–C₄ alkyl and halo is Cl, Br, F or I.

37. The composition of claim 34, wherein said precursor comprises a compound selected from the group consisting of:

[(Me₃Si)₂N]₅₋ᵦMXᵦ wherein b is 2 or 3, X is Cl, Br, F or I, and M is Nb; and

[(Me₃Si)₂N]₆₋ᵦWXᵦ wherein b is 1 or 2, and X is Cl, Br, F or I.

38. The composition of claim 34, further comprising a boron source reagent, wherein said boron source reagent comprises a borane selected from the group consisting of borane, decaborane, alkylboranes and amidoboranes.

39. The composition of claim 34, further comprising a compound of formula (II):

wherein:
X is Cl or Br;
m, n and y can each be the same as or different from each other, and each is independently from 0 to 3 inclusive; and
R and R' are the same as or different from one another, and each is independently selected from the group of H, C₁–C₄ alkyl, and C₃–C₆ cycloalkyl.

40. The composition of claim 39, wherein said compound of formula (II) is selected from the group consisting of:
ClSiH₃;
H₂SiCl₂;
Me₃SiCl; and
t-Bu₂SiCl₂.

41. The composition of claim 34, wherein said precursor comprises a compound selected from the group consisting of:
(EtHN)₆₋ᵦWXᵦ wherein b is from 1 to 2 inclusive;
(EtMeN)₆₋ᵦWXᵦ wherein b is from 1 to 2 inclusive;
(Me₂N)₆₋ᵦWXᵦ wherein b is from 1 to 2 inclusive;
(Et₂N)₆₋ᵦWXᵦ wherein b is from 1 to 2 inclusive;
(EtHN)₅₋ᵦMXᵦ wherein M is Ta or Nb, and b is 1 or 2;
(EtMeN)₅₋ᵦMXᵦ wherein M is Ta or Nb, and b is 1 or 2;
(Me₂N)₅₋ᵦMXᵦ wherein M is Ta or Nb, and b is 1 or 2;
(Et₂N)₅₋ᵦMXᵦ wherein M is Ta or Nb, and b is 1 or 2;
(EtHN)₄₋ᵦTiXᵦ wherein b is from 1 to 2 inclusive;
(EtMeN)₄₋ᵦTiXᵦ wherein b is from 1 to 2 inclusive;
(Me₂N)₄₋ᵦTiXᵦ wherein b is from 1 to 2 inclusive;
(Et₂N)₄₋ᵦTiXᵦ wherein b is from 1 to 2 inclusive;
[(Me₃Si)₂N]₅₋ᵦMXᵦ wherein b is 2 or 3, X is Cl, Br, F or I, and M is Nb; and
[(Me₃Si)₂N]₆₋ᵦWXᵦ wherein b is 1 or 2, and X is Cl, Br, F or I.

42. A metalorganic precursor of formula (I):

wherein:
M is selected from the group of Ta and Ti;
a is a number equal to the valence of M;
$1 \leq b \leq (a-1)$;
R₁ and R₂ can be the same as or different from one another, and are each independently selected from the group of H, C₁–C₄ alkyl, C₃–C₆ cycloalkyl, and R⁰₃Si, where each R⁰ can be the same or different and each R⁰ is independently selected from H and C₁–C₄ alkyl provided that at least one of R⁰ is H; and
X is selected from the group of chlorine, fluorine, bromine and iodine;
but excluding compounds of the formula (Me₂N)₄₋ᵦTiXᵦ wherein b is from 1 to 2 inclusive.

43. A metalorganic precursor composition comprising a precursor compound of formula (I):

wherein:
M is selected from the group of Ta and Ti;
a is a number equal to the valence of M;
$1 \leq b \leq (a-1)$;
R₁ and R₂ can be the same as or different from one another, and are each independently selected from the group of H, C₁–C₄ alkyl, C₃–C₆ cycloalkyl, and R⁰₃Si, where each R⁰ can be the same or different and each R⁰ is independently selected from H and C₁–C₄ alkyl provided that at least one of R⁰ is H; and
X is selected from the group of chlorine, fluorine, bromine and iodine,
but excluding compounds of the formula (Me₂N)₄₋ᵦTiXᵦ wherein b is from 1 to 2 inclusive.

* * * * *

UNITED STATES PATENT AND TRADEMARK OFFICE
CERTIFICATE OF CORRECTION

| | |
|---|---|
| PATENT NO. | : 7,208,427 B2 |
| APPLICATION NO. | : 10/643110 |
| DATED | : April 24, 2007 |
| INVENTOR(S) | : Roeder et al. |

It is certified that error appears in the above-identified patent and that said Letters Patent is hereby corrected as shown below:

Column 10, line 40 (claim 1): "H $C_1 - C_4$ alkyl" should be -- H, $C_1 - C_4$ alkyl --

Column 10, lines 41-42: " the same different" should be -- the same or different --

Signed and Sealed this

Twenty-sixth Day of June, 2007

JON W. DUDAS
*Director of the United States Patent and Trademark Office*